United States Patent [19]
Pipes et al.

[11] Patent Number: 6,113,885
[45] Date of Patent: Sep. 5, 2000

[54] POLYOLEFIN PACKAGED DENTIFRICE HAVING REDUCED FLAVOR LOSS

[75] Inventors: Dennis T. Pipes, Asbury; Edward S. Hodgetts, Kendall Park; Nicholas J. Sparacio, Edison, all of N.J.

[73] Assignee: Colgate Palmolive Company, New York, N.Y.

[21] Appl. No.: 09/213,628

[22] Filed: Dec. 18, 1998

[51] Int. Cl.⁷ .............................. A61K 7/16; B65D 35/08; B65D 35/14; B32B 15/08
[52] U.S. Cl. ............................................. 424/49; 222/107
[58] Field of Search ................. 424/49–58, 401; 222/107

[56] References Cited

U.S. PATENT DOCUMENTS

| | | | |
|---|---|---|---|
| 3,932,604 | 1/1976 | Barth | 424/49 |
| 3,957,559 | 5/1976 | Hoffman . | |
| 3,970,747 | 7/1976 | Barth | 424/52 |
| 4,526,823 | 7/1985 | Farrell et al. . | |
| 4,539,259 | 9/1985 | Zuscik . | |
| 4,551,371 | 11/1985 | Eckstein . | |
| 4,595,612 | 6/1986 | Tavss et al. . | |
| 4,595,613 | 6/1986 | Tavss et al. . | |
| 4,608,285 | 8/1986 | Tavss et al. . | |
| 4,620,956 | 11/1986 | Hamer . | |
| 4,693,395 | 9/1987 | Tavss et al. . | |
| 4,693,396 | 9/1987 | Tavss et al. . | |
| 4,838,461 | 6/1989 | Santer et al. . | |
| 4,894,267 | 1/1990 | Bettle . | |
| 4,977,004 | 12/1990 | Bettle . | |
| 5,234,688 | 8/1993 | Gaffar . | |
| 5,238,148 | 8/1993 | Holoubek et al. . | |
| 5,260,062 | 11/1993 | Gaffar . | |
| 5,320,889 | 6/1994 | Bettle . | |
| 5,322,658 | 6/1994 | Holoubek et al. . | |
| 5,407,742 | 4/1995 | Tavss et al. . | |
| 5,484,083 | 1/1996 | Joulia . | |
| 5,565,248 | 10/1996 | Plester . | |
| 5,571,470 | 11/1996 | Plester . | |
| 5,707,691 | 1/1998 | Plester . | |
| 5,816,451 | 10/1998 | Renault . | |
| 5,849,366 | 12/1998 | Plester . | |

FOREIGN PATENT DOCUMENTS

| | | |
|---|---|---|
| 351 925 | 1/1990 | European Pat. Off. . |
| 351 926 | 1/1990 | European Pat. Off. . |
| 444 835 | 9/1991 | European Pat. Off. . |
| 665 102 | 8/1995 | European Pat. Off. . |
| 2206530 | 1/1989 | United Kingdom . |
| 2206531 | 1/1989 | United Kingdom . |
| 2206532 | 1/1989 | United Kingdom . |

OTHER PUBLICATIONS

Tavss et al (I) J. Chromatogr. 438(2):281–289, 1988.
Taverna et al J. Assoc. Off. Anal. Chem. 73(2):206–210, 1990.
Becker et al II Parfuem. Kosmet. 68(5):268–272, 274–276, 278 (HDPE), 1987.
Doege et al Pharmazie 39(6):423–424 (HDPE), 1984.
Fouraste et al Plant Med Phytother. (17)2:96–106, 1983.
Becker et al I Dtsch. Lebensm. Rundsch. 79(8):257–266, 1983.
Artem'ev et al (II) Farmatsiya 29(6) 15–17 HDPE, 1980.
Skaletzki et al Pharmazie 38(6):392–395, 1983.
Basquin et al Parfums Cosmet. Savons Fr. 2(4):170–173 HDPE, 1973.
Artem'ev Aptechn. Delo 15(6):29–34 HDPE, 1966.

*Primary Examiner*—Shep K. Rose
*Attorney, Agent, or Firm*—Paul Shapiro

[57] ABSTRACT

A dentifrice packaged in a polyolefin container, the dentifrice having improved stability against flavor loss by adsorption into the polyolefin substrate, the dentifrice containing at least about 30% by weight sorbitol on a neat basis as the sole liquid humectant and no more than about 23% by weight water.

14 Claims, No Drawings

POLYOLEFIN PACKAGED DENTIFRICE HAVING REDUCED FLAVOR LOSS

BACKGROUND OF THE INVENTION

1. Field of the Invention

This invention relates to reduction of flavor permeation and absorption onto the walls of polyolefin plastic materials used for the packaging of dentifrice products.

2. The Prior Art

Tubes formed of polyolefin materials such as polyethylene have enjoyed wide commercial success in the packaging of many products. However, polyolefin materials such as polyethylene and particularly high density polyethylene are permeable to flavor oils and due to this permeability dentifrice compositions during storage in polyolefin tubes encounter a loss of flavor oils rendering the dentifrice less palatable. Manufacturers of dentifrices have attempted to minimize the flavor absorptive loss by using less permeable plastic tube materials wherever possible, but cost constraints limit the use of these materials in areas of the world where cost is a major factor in the purchase of the toothpaste product. Toothpaste manufacturers have increased the level of flavor in their products, to make up for the flavor lost in the permeable polyolefin plastic tubes but the extra cost of the additional flavor militates against this solution to the problem.

An ideal least cost remedy for the flavor absorption problem would be to prepare the dentifrice formulation in a simple manner whereby migration of the flavor onto the inner surface of the tube walls would be minimized.

SUMMARY OF THE INVENTION

In accordance with the present invention it has been found that the flavor loss from a polyolefin packaged dentifrice is reduced when the liquid content of the dentifrice is comprised of sorbitol as the sole humectant which is present in the dentifrice in an amount at least about 30% by weight on a neat basis and water is present in an amount of no more than about 23% by weight.

DESCRIPTION OF THE PREFERRED EMBODIMENTS

The dentifrice of the present invention contains about 10 to about 23% by weight water and preferably about 15 to about 21% by weight water and about 30 to about 45% by weight sorbitol on a neat basis and preferably about 33 to about 42% by weight sorbitol on a neat basis.

The dentifrice of the present invention may be in the form of a paste or gel and contain in addition to sorbitol and water, a flavor oil and substantial proportions of a surface active agent, polishing gel and thickening agent.

Any suitable flavor oil or mixture thereof may be used in this invention. Examples of flavor oils include oils of spearmint, peppermint, wintergreen, clove, sage, eucalyptus, cinnamon, lemon and orange. The flavoring oils are water insoluble and are emulsified into the dentifrice formulation under moderate agitation in amounts of 0.01 to 2% by weight and preferably about 0.5 to about 1% by weight.

The surface active agent present in the dentifrice is generally anionic or nonionic. Anionics are the most preferred. Among the useful anionic surface active agents are the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, the substantially saturated higher aliphatic acyl amides of lower aliphatic aminocarboxylic acid alkali metal salts, such as those having 12 to 16 carbon atoms in the fatty acyl radicals. Sodium lauryl sulfate (SLS) is a preferred anionic surfactant.

Nonionic surface active agents useful in the practice of the present invention include those containing a chain of lower alkylene oxide, e.g., ethylene oxide, propylene oxide, in which there are present from 10 to 100 or more moles of lower alkylene oxide. Among such materials are the block copolymers of ethylene oxide, propylene oxide and propylene glycol, sold as Pluronics.

The surface active agents constitute about 0.5 to about 5% by weight and preferably about 1 to about 3% by weight of the dentifrice composition.

Suitable polishing agents useful to prepare the dentifrice compositions of the present invention include anhydrous dicalcium phosphate, dicalcium phosphate dihydrate, crystalline silica, colloidal silica, complex aluminosilicates, aluminum hydroxide (including alumina trihydrate or hydrated alumina), calcined alumina, calcium carbonate, calcium pyrophosphate, bentonite, talc, sodium bicarbonate, calcium silicate, calcium aluminate, aluminum silicate, and silica xerogels. The polishing agents are included in the dentifrice composition of the present invention at concentrations of about 20 to about 70% by weight and preferably about 35 to about 60% by weight of the dentifrice composition.

Thickening agents include natural and synthetic gum-like materials, e.g., carrageenan gum, gum tragacanth, sodium carboxymethylcellulose, polyvinylpyrrolidone, xanthan gum, or starch. Carrageenan gum and sodium carboxymethylcellulose, are preferred gelling agents. The gelling agent content is usually in an amount up to about 10% and preferably about 0.3 to about 5% by weight of the dentifrice composition. Colloidal silica aerogels which include Syloids 244 and 266 and Aerosil, and the pyrogenic silica sold as Cab—O—Sil may be also used as gelling and thickening agents.

Sweetening agents which may be present in the dentifrice composition include lactose, maltose, sorbitol, xylitol, sodium cyclamate, perrillartine and saccharine. Suitably the sweetening agent comprises from about 0.01 to 1% by weight of the dentifrice composition.

Various other ingredients may also be used to prepare the dentifrice composition. Examples thereof are fluorine-containing anticaries compounds such as sodium fluoride, stannous fluoride, sodium hexafluorosilicate and sodium monoflurophosphate. These components are present in the dentifrice composition in an amount of about 0.1 to about 5% by weight of the dentifrice composition.

Other additives include preservatives such as sodium benzoate, chlorophyll compounds, silicones, vitamins such as B6, B 12, E and K, silicones, peroxide compounds such as urea peroxide, hydrogen peroxide, calcium peroxide antibacterial agents such as Triclosan, coloring agents such as $TiO_2$, anticalculus agents such as tetrasodium pyrophosphate, tetrapotassium pyrophosphate, sodium tripolyphosphate and mixtures thereof. These additives may be used in amounts which do not adversely affect the properties and characteristics of the dentifrice in accordance with the present invention. Each constituent may be present in minimal amounts of up to 7% by weight.

The dentifrice formulations of the present invention are formulated to a creamy mass of desired consistency, which is extrudable from a collapsible tube formed from a polyolefin resin material such as low density polyethylene (LDPE), high density polyethylene (HDPE), polypropylene and ethylene/propylene copolymers.

The dentifrice of this invention is prepared by conventional methods of making toothpaste, and dental creams. More specifically, to prepare a dentifrice of the present invention, generally sorbitol is dispersed with a sweetener and water in a conventional mixer, until the mixture becomes a homogeneous gel phase. Into the gel phase are added a pigment such as $TiO_2$, any acid or base required to adjust the pH, and any fluoride anticaries agents, such as sodium fluoride. These ingredients are mixed until a homogeneous phase is obtained, whereupon a polishing agent is mixed into the gel phase. The mixture is then transferred to a high speed/vacuum mixer, wherein a thickener, flavor, and surfactant are added. The resultant composition is then mixed at high speed under vacuum of from about 20 to 100mm of Hg. The resultant product is in each case a homogeneous, semi-solid extrudable paste product which is then tubed in a polyethylene container tube.

The following example is further illustrative of the nature of the present invention, but it is understood that the invention is not limited thereto. The compositions are prepared in the manner and all amounts and proportions referred to herein and in the appended claims are by weight unless otherwise specified.

EXAMPLE

A series of dentifrice compositions designated "A", "B" and "C" of the present invention were prepared having the ingredients listed in Table I below.

TABLE I

| Composition | A | | B | | C | |
|---|---|---|---|---|---|---|
| Ingredient | Weight % | | | | | |
| Sorbitol (70%) | 38.50 sorbitol | 16.5 water | 40.60 sorbitol | 17.4 water | 35.00 sorbitol | 15.00 water |
| Water (deionized) | 2.89 | | 2.89 | | 0.89 | |
| Silica polishing agent | 19.25 | | 17.50 | | 22.50 | |
| Dicalcium phosphate dihydrate | 19.25 | | 17.50 | | 22.50 | |
| $TiO_2$ | 0.00 | | 0.50 | | 0.50 | |
| Sodium lauryl sulfate | 1.50 | | 1.50 | | 1.50 | |
| Sodium monofluorophosphate | 0.76 | | 0.76 | | 0.76 | |
| Na saccharin | 0.20 | | 0.20 | | 0.20 | |
| Carrageenan gum | 0.25 | | 0.25 | | 0.25 | |
| Flavor oil | 0.90 | | 0.90 | | 0.90 | |
| Total Water | | 19.39 | | 20.29 | | 15.89 |

For purposes of comparison, the procedure of the Example was repeated, except the water concentration of the dentifrice composition was increased to concentrations greater than 3% by weight. The ingredients of these comparative compositions are listed in Table II below.

TABLE II

COMPARATIVE DENTIFRICE COMPOSITIONS

| Composition | D | | E | | F | |
|---|---|---|---|---|---|---|
| Ingredient | Weight % | | | | | |
| Sorbitol (70%) | 40.60 sorbitol | 17.4 water | 45.50 sorbitol | 19.5 water | 50.40 sorbitol | 21.6 water |
| Water | 22.11 | | 15.11 | | 4.11 | |
| Silica polishing agent | 12.00 | | 12.00 | | 16.00 | |
| Sodium lauryl sulfate | 1.50 | | 1.50 | | 1.50 | |
| Coliodial silica thickener | 4.0 | | 4.0 | | 4.0 | |
| Na saccharin | 0.2 | | 0.2 | | 0.2 | |
| NaF | 0.24 | | 0.24 | | 0.24 | |
| $TiO_2$ | 0.50 | | 0.50 | | 0.50 | |
| Carrageenangum | 0.55 | | 0.55 | | 0.55 | |
| Flavor oil | 0.90 | | 0.90 | | 0.90 | |
| Total Water | | 39.51 | | 34.61 | | 25.71 |

The dentifrices disclosed in Tables I and II were packaged in sealed, high density polyethylene tubes and the effect on flavor absorption under accelerated aging conditions (6 weeks at 120° F.) was determined. Flavor loss after the 6 week aging period was measured instrumentally using a gas chromatograph which measured the level of flavor in the dentifrice prior to aging (initial) and after aging (final). Flavor loss was calculated by the equation:

$$\frac{(\text{Initial flavor level} - \text{final flavor level}) \times 100\%}{\text{Initial flavor level}}$$

The results of the aging tests are recorded in Table III below.

TABLE III

| Composition | Initial Conc. (%) | Conc. After Aging (%) | % Flavor Loss |
|---|---|---|---|
| A | 0.85 | 0.73 | 14 |
| B | 0.87 | 0.73 | 16 |
| C | 0.86 | 0.71 | 17 |
| D | 0.912* | 0.46* | 50 |
| E | 0.894* | 0.52* | 42 |
| F | 0.899* | 0.64* | 29 |

*Average of six replicates

The results recorded in Table III indicate that dentifrice compositions of the present invention (Compositions A–C) encountered substantially less flavor loss (14–17%) than the comparative compositions (D, E, F) which encountered flavor losses of 29–50% when containing water concentrations above about 23% by weight, (that is, 26–40% by weight) demonstrating that the unique combination of sorbitol as the sole humectant and water concentrations of less than about 23% by weight provided unexpected inhibition of flavor loss from the dentifrice when packaged in high density polyethylene tubes.

What is claimed is:

1. A dentifrice packaged in a container in which the inner contact surface is formed from a polyolefin material, the dentifrice having improved stability against flavor loss by adsorption into the contact surface, the dentifrice comprising at least about 30% by weight sorbitol on a neat basis as the sole liquid humectant and no more than about 23% by weight water.

2. The dentifrice of claim 1 wherein the polyolefin is high density polyethylene.

3. The dentifrice of claim 1 wherein the sorbitol on a neat basis is present in the dentifrice in an amount of about 30 to about 45% by weight.

4. The dentifrice of claim 1 wherein the sorbitol on a neat basis is present in the dentifrice in an amount of about 33 to about 42% by weight.

5. The dentifrice of claim 1 wherein the water is present in the dentifrice in an amount of about 10 to about 23% by weight.

6. The dentifrice of claim 1 wherein the water is present in the dentifrice in an amount of about 15 to about 21% by weight.

7. The dentifrice of claim 1 wherein the flavor oil is present in the dentifrice in an amount of about 0.01 to about 1% by weight.

8. A method of preparing a dentifrice having improved stability against flavor loss by adsorption when packaged in a container in which the inner contact surface is formed from a polyolefin material, comprising preparing a dentifrice containing at least about 30% by weight sorbitol on a neat basis as the sole humectant and no more than about 23% by weight water and then filling the container with the dentifrice.

9. The method of claim 8 wherein the polyolefin material is high density polyethylene.

10. The method of claim 9 wherein the sorbitol on a neat basis is present in the dentifrice in an amount of about 30 to about 45% by weight.

11. The method of claim 9 wherein the water is present in the dentifrice in an amount of about 10 to about 23% by weight.

12. The method of claim 9 wherein the sorbitol on a neat basis is present in the dentifrice in an amount of about 33 to about 42% by weight.

13. The method of claim 9 wherein the water is present in the dentifrice in an amount of about 15 to about 21% by weight.

14. The method of claim 9 wherein the flavor oil is present in the dentifrice in an amount of about 0.01 to about 1% by weight.

* * * * *